Reissued July 13, 1937

Re. 20,447

UNITED STATES PATENT OFFICE 20,447

PRODUCTION OF ALCOHOLS

Walther Schrauth, Berlin-Dahlem, and Theodor Böttler, Rodleben, near Rosslau, Germany, assignors, by mesne assignments, to "Unichem" Chemikalien Handels A.-G., Zurich, Switzerland, a corporation of Switzerland No Drawing. Original No. 2,023,383, dated December 3, 1935, Serial No. 609,034, May 3, 1932. Application for reissue October 16, 1936, Serial No. 105,936. In Germany February 22, 1932

12 Claims. (Cl. 260—156)

The present invention has for an object to provide an improved process for hydrogenation and splitting of organic compounds and especially high molecular aliphatic compounds to produce lower molecular compounds.

The invention has further for an object to provide an improved process for producing alcohols from high molecular aliphatic esters.

In the known processes for hydrogenation of coal deposits, coal distillates, tars, mineral oils, fats and the like these products are heated to higher temperatures under hydrogen pressure in the presence of metals or metal oxides or similar contact agents. Owing to their solid state of aggregation such catalysts often give rise to troubles in the operation of continuous processes of production, as they are liable to destroy the packings of the pumping lines when pumped together with the products of the hydrogenation process, or their replacement in stationary apparatus in case of toxication or choking can only be effected with great trouble and loss of time.

It is now found that the metal salts of organic acids of high molecular weight—with the exception of the salts of alkalis, alkaline earths, and noble metals—can be used with great success as catalysts for hydrogenation processes operating under high pressure and at increased temperatures such as the hydrogenation and splitting of coal deposits, coal distillates, tars, mineral oils, fats, and the like, the said salts being soluble or emulsive in the reaction mixture of the hydrogenation and splitting process as well as in the reaction products, so that they can be transported together with the substances to be hydrogenated in most simple and convenient manner into the reaction chamber without damaging the pressure pumps. Such catalysts are for instance the known dry substances used in the manufacture of lacquers: copper, zinc, lead, manganese, cobalt, mercury salts of palmitic, stearic, linseed-oil, colophonic or naphthenic acids.

Other heavy metal salts of organic acids, however, may likewise be used, for instance, chromous cocoic acid, if they are soluble or emulsive in the substances to be hydrogenated.

During the process the contact-agents are freed under pressure and heat from the metal salts in fine distribution, resulting in an extraordinary acceleration of the hydrogenation and splitting process.

*Example 1.*—If 1000 parts of naphthalene, in which 5 parts of nickel oleate are dissolved, are heated in an autoclave under an initial hydrogen pressure of 80 atm. to a temperature of 450°–480° C., in the course of 2–3 hours 700–800 parts of reaction products are formed, consisting mostly of benzol homologues, 80% of which distil over below 180° C. Instead of nickel oleate, cobalt resinate or mixtures of these alone or for instance with manganic laurate can likewise be employed.

*Example 2.*—In order to convert mineral oils with high boiling points, such as panuco oil or coal tar-peat into benzine or benzene hydrocarbons with low boiling points, 3–5% of resinate of mercury or a mixture of equal parts of linseed-acidoleous copper or resinate of zinc or palmitate of aluminum are added to the initial substances, then heated till a homogeneous, easily fusible mixture is obtained, which is then pressed by hydrogen at 200 atm. pressure into the reaction chamber and heated to 400–500° C. Owing to the extremely fine distribution of the catalyst, the splitting is effected in a short time, resulting in hydrocarbons boiling below 200° or 300° C. and practically no residue.

*Example 3.*—If a mixture of 20 parts of copper carbonate and 100 parts of oleic acid are added to 1000 parts of cocoanut fat, supplying a dark green liquid when heated, and the reaction mixture is heated to 280°–300° C. under a hydrogen pressure of 100–200 atm. a nearly quantitative yield of the corresponding cocoa-nut fatty alcohols is obtained.

We claim:—

1. The process of producing high molecular alcohol which comprises adding to natural fats a hydrogenation catalyst of the group consisting of copper, zinc, lead, manganese, cobalt and mercury, salts of palmitic, stearic, linseed oil, colophonic or naphthenic acids and chromous cocoic acid and subjecting the mixture to the action of hydrogen under a pressure of about 100 to 200 atmospheres and at a temperature of about 280 to 300° C. until the esters are separated into alcohols and acids and the acids are reduced to alcohol.

2. The process of producing high molecular alcohol which comprises adding to natural fats a hydrogenation catalyst of the group consisting of copper, zinc, lead, manganese, cobalt and mercury, salts of palmitic, stearic, linseed oil, colophonic or naphthenic acids and chromous cocoic acid and subjecting the mixture to the action of hydrogen at a pressure of about 80 to 200 atmospheres and at a temperature of about 280 to 480° C.

3. The process of producing high molecular alcohol which comprises subjecting a mixture of cocoanut fat and copper oleate to the action of hydrogen under a pressure approximating 100 to 200 atmospheres and at a temperature approximating 280 to 300° C.

4. The process of producing high molecular alcohol which comprises adding to natural fats, nickel oleate and subjecting the mixture to the action of hydrogen at a pressure approximating 80 atmospheres and at a temperature approximating 450 to 480° C.

5. The process of producing high molecular alcohol which comprises adding to natural fats the copper salt of linseed oil acid and subjecting the mixture to the action of hydrogen at a pressure approximating 200 atmospheres and at a temperature approximating 400 to 500° C.

6. The process of producing high molecular alcohol which comprises adding to natural fats a hydrogenation catalyst consisting of a copper salt of an organic acid of high molecular weight having approximately 12 to 18 carbon atoms in the molecule and subjecting the mixture to the action of hydrogen at a pressure of about 80 to 200 atmospheres and at a temperature of about 280 to 480° C.

7. The process of producing high molecular alcohol which comprises adding to natural fats a hydrogenation catalyst of the group consisting of copper, zinc, lead, manganese, cobalt and mercury, salts of palmitic, stearic, linseed oil, colophonic or naphthenic acids and chromous cocoic acid and subjecting the mixture to the action of hydrogen at a pressure of about 80 to 200 atmospheres and at a temperature of about 280 to 480° C. until the esters are split into alcohols and acids and the acids are reduced to alcohols.

8. The process of producing high molecular alcohol which comprises adding to natural fats, nickel oleate and subjecting the mixture to the action of hydrogen at a pressure approximating 80 atmospheres and at a temperature approximating 450 to 480° C. until the esters are split into alcohols and acids and the acids are reduced to alcohols.

9. The process of producing high molecular alcohol which comprises adding to natural fats a hydrogenation catalyst consisting of a copper salt of an organic acid of high molecular weight having approximately 12 to 18 carbon atoms in the molecule and subjecting the mixture to the action of hydrogen at a pressure of about 80 to 200 atmospheres and at a temperature of about 280 to 480° C. until the esters are split into alcohols and acids and the acids are reduced to alcohols.

10. The process of splitting esters which comprises adding to natural fats a hydrogenation catalyst of the group consisting of copper, zinc, lead, manganese, cobalt and mercury, salts of palmitic, stearic, linseed oil, colophonic or naphthenic acids and chromous cocoic acid and subjecting the mixture to the action of hydrogen at a pressure of about 80 to 200 atmospheres and at a temperature of about 280 to 480° C.

11. The process of splitting high molecular aliphatic compounds to produce low molecular aliphatic compounds therefrom which comprises adding to natural fats a hydrogenation catalyst of the group consisting of copper, zinc, lead, manganese, cobalt and mercury, salts of palmitic, stearic, linseed oil, colophonic or naphthenic acids and chromous cocoic acid and subjecting the mixture to the action of hydrogen at a pressure of about 80 to 200 atmospheres and at a temperature of about 280 to 480° C.

12. The process of splitting high molecular organic compounds to produce low molecular organic compounds therefrom which comprises adding to natural fats a hydrogenation catalyst of the group consisting of copper, zinc, lead, manganese, cobalt and mercury, salts of palmitic, stearic, linseed oil, colophonic or naphthenic acids and chromous cocoic acid and subjecting the mixture to the action of hydrogen at a pressure of about 80 to 200 atmospheres and at a temperature of about 280 to 480° C.

WALTHER SCHRAUTH.
THEODOR BÖTTLER.